US011030746B2

(12) United States Patent
Wang et al.

(10) Patent No.: US 11,030,746 B2
(45) Date of Patent: Jun. 8, 2021

(54) ASSISTED DENTAL BEAUTIFICATION METHOD AND APPARATUS FOR IMPLEMENTING THE SAME

(71) Applicant: Chengdu Besmile Medical Technology Co., Ltd., Chengdu (CN)

(72) Inventors: Changjian Wang, Chengdu (CN); Xinzhang Yan, Chengdu (CN); Hongbin Cai, Chengdu (CN); Guanghui Lu, Chengdu (CN); Shuai Liu, Chengdu (CN); Dengkai Zhang, Chengdu (CN)

(73) Assignee: Chengdu Besmile Medical Technology Co., Ltd., Chengdu (CN)

( * ) Notice: Subject to any disclaimer, the term of this patent is extended or adjusted under 35 U.S.C. 154(b) by 2 days.

(21) Appl. No.: 16/630,836

(22) PCT Filed: Jan. 8, 2019

(86) PCT No.: PCT/CN2019/070762
§ 371 (c)(1),
(2) Date: Jan. 13, 2020

(87) PCT Pub. No.: WO2019/141106
PCT Pub. Date: Jul. 25, 2019

(65) Prior Publication Data
US 2020/0143541 A1 May 7, 2020

(30) Foreign Application Priority Data

Jan. 18, 2018 (CN) .......................... 201810049574.6
Feb. 28, 2018 (CN) .......................... 201810165138.5

(51) Int. Cl.
*G06T 7/00* (2017.01)
*G06T 7/62* (2017.01)
(Continued)

(52) U.S. Cl.
CPC ......... *G06T 7/0014* (2013.01); *G06N 3/0481* (2013.01); *G06T 3/40* (2013.01);
(Continued)

(58) Field of Classification Search
None
See application file for complete search history.

(56) References Cited

U.S. PATENT DOCUMENTS 8,740,614 B2   6/2014   Wen et al.
9,939,999 B2   4/2018   Wen et al.
(Continued)

FOREIGN PATENT DOCUMENTS

CN   101616637 A   12/2009
CN   101862175 A   10/2010
(Continued)

OTHER PUBLICATIONS

International Search Report; International Searching Authority/CN dated Mar. 28, 2019; International Application No. PCT/CN2019/070762; 5 pgs.; National Intellectual Property Administration, PRC (ISA/CN); Beijing, China.
(Continued)

*Primary Examiner* — Jiangeng Sun
(74) *Attorney, Agent, or Firm* — Andrew D. Fortney; Central California IP Group, P.C.

(57) ABSTRACT

The disclosure relates to field of aesthetic dental technology, more particularly relates to a C/S architecture-based dental beautification AR smart assistance method and apparatus. Specifically, an auxiliary method for dental beautification may include obtaining information; processing the information and obtaining the results of information processing; and generating and displaying the beautification schemes according to the results of information processing. A terminal device for dental beautification, including a memory for (Continued)

storing computer program code and a processor for executing computer program code stored in the memory, is also disclosed. The dental beautification method and apparatus can provide the teeth reference effect after beautification in advance, such as providing reference pictures and videos. Patients can participate in the process of designing the plans, and can also provide different beautification plans for selection, which effectively improves the enthusiasm of patients for dental beautification.

19 Claims, 9 Drawing Sheets

(51) Int. Cl.
 *G06N 3/04* (2006.01)
 *G06T 3/40* (2006.01)
(52) U.S. Cl.
 CPC ...... *G06T 7/62* (2017.01); *G06T 2207/10016* (2013.01); *G06T 2207/20084* (2013.01); *G06T 2207/20212* (2013.01); *G06T 2207/30036* (2013.01)

(56) References Cited

U.S. PATENT DOCUMENTS

| | | | |
|---|---|---|---|
| 2002/0055800 A1 | 5/2002 | Nikolskiy et al. | |
| 2002/0188478 A1 | 12/2002 | Breeland et al. | |
| 2004/0136580 A1 | 7/2004 | Matsumiya et al. | |
| 2006/0275731 A1 | 12/2006 | Wen et al. | |
| 2009/0132283 A1 | 5/2009 | Hara et al. | |
| 2009/0286196 A1 | 11/2009 | Wen et al. | |
| 2013/0286174 A1 | 10/2013 | Urakabe | |
| 2014/0229878 A1 | 8/2014 | Wen et al. | |
| 2015/0320320 A1* | 11/2015 | Kopelman | A61C 9/0053 433/24 |
| 2017/0049330 A1* | 2/2017 | Kopelman | G06T 7/579 |
| 2017/0300207 A1 | 10/2017 | Wen et al. | |
| 2018/0005371 A1* | 1/2018 | Sabina | G06T 7/11 |

FOREIGN PATENT DOCUMENTS

| | | | |
|---|---|---|---|
| CN | 106491068 A | 3/2017 | |
| CN | 107126275 A | 9/2017 | |
| CN | 108305684 A | 7/2018 | |
| CN | 108305689 A | 7/2018 | |
| EP | 1434028 A1 | 6/2004 | |
| JP | 2010214055 A | 9/2010 | |
| WO | 2007063980 A1 | 6/2007 | |
| WO | WO-2018230873 A1 * | 12/2018 | A61C 13/082 |

OTHER PUBLICATIONS

Search Report on International Application No. PCT/CN2019/070762; dated Sep. 17, 2019; 6 pgs.; National Intellectual Property Administration, PRC (ISA/CN); Beijing, China.

* cited by examiner

|   |   |   |   |   |   |   |   |   |   |   |   |   |   |   |   |
|---|---|---|---|---|---|---|---|---|---|---|---|---|---|---|---|
|   |   |   | the right maxillary |   |   |   |   |   |   |   | the left maxillary |   |   |   |   |
| 18 | 17 | 16 | 15 | 14 | 13 | 12 | 11 | 21 | 22 | 23 | 24 | 25 | 26 | 27 | 28 |
| 48 | 47 | 46 | 45 | 44 | 43 | 42 | 41 | 31 | 32 | 33 | 34 | 35 | 36 | 37 | 38 |
|   |   |   | the right mandibular |   |   |   |   |   |   |   | the left mandibular |   |   |   |   |

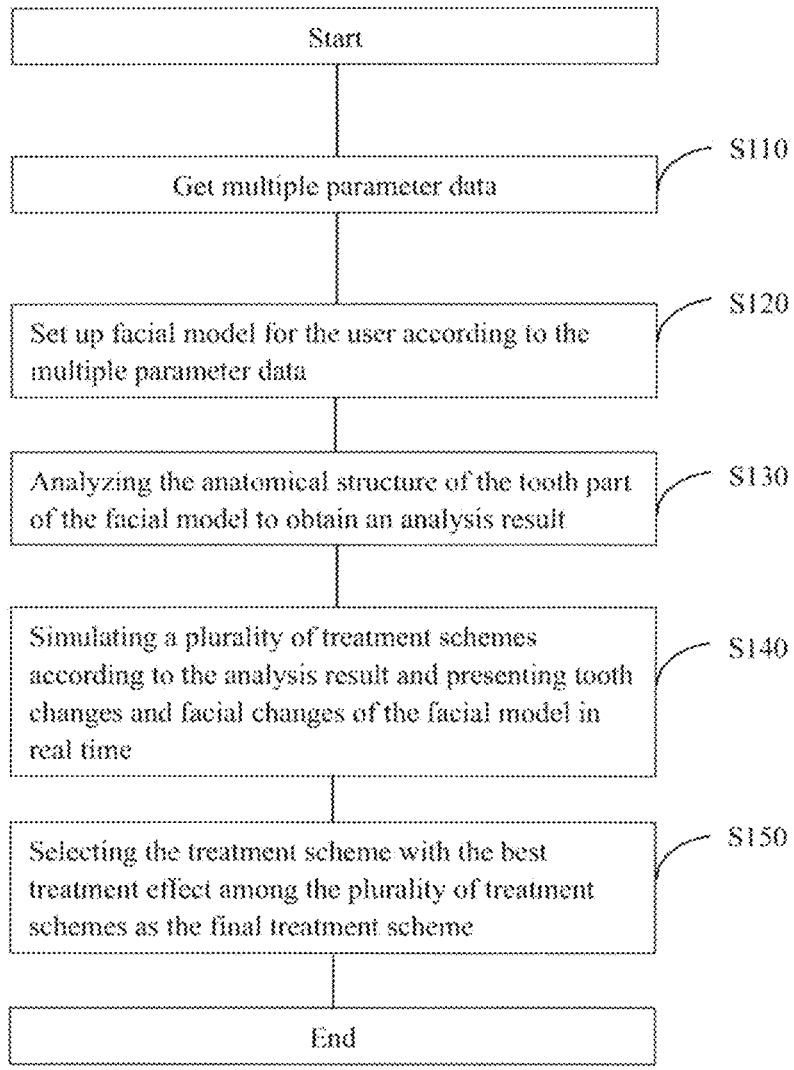

US 11,030,746 B2

ASSISTED DENTAL BEAUTIFICATION METHOD AND APPARATUS FOR IMPLEMENTING THE SAME

CROSS REFERENCE TO RELATED APPLICATIONS

The present application is a national phase application of International Application No. PCT/CN2019/070762, filed Jan. 8, 2019, which claims priority to Chinese Pat. Appl. Nos. 201810049574.6 and 201810165138.5, filed respectively on Jan. 18, 2018 and Feb. 28, 2018.

TECHNICAL FIELD

The present invention relates to field of aesthetic dental technology, more particularly relates to a C/S architecture-based dental beautification AR smart assistance method and apparatus.

BACKGROUND OF THE INVENTION

Dental beautification comprises tooth restoration, correction, whitening, tooth movement and other tooth cosmetic or plastic projects. At present, dental beautification is generally time-consuming and expensive, and patients are more likely not to accept beautification under the condition of uncertain visual effects of the beautified teeth. At the same time, since the beautification effect cannot be seen in advance and the patients cannot directly participate in the beautification scheme design process, the patients can basically only rely on oral communication with doctors to select the scheme, which may also lead to the patients' dissatisfaction with the final beautification result. If patients can participate in the process of designing their own tooth beautification schemes, and doctors can show patients the effects of various beautification schemes in advance, allowing patients to choose among several beautification schemes provided by dentists, the enthusiasm of patients to accept beautification will be greatly improved. At present, facing the above problems, the solution is mainly to replace the patient's tooth pictures and videos on the PC. However, the PC has problems such as inconvenience in operation, insufficient portability and flexibility. If the system is directly deployed on a smart terminal, there are also shortcomings such as insufficient computing power and insufficient storage space.

SUMMARY OF THE INVENTION

An object of the present invention is to provide a C/S architecture-based dental beautification AR smart assistance method and apparatus.

A dental beautification method is adopted to achieve the above-mentioned object, comprising the following steps:

(1) obtaining information required for dental beautification;

(2) processing the information, wherein the processing comprises at least one of analysis, calculation and matching, and obtaining an information processing result;

(3) generating a beautification scheme according to the information processing result;

(4) displaying and beautifying the scheme.

The method is based on a user terminal and a server, and the user terminal and the server communicate with each other.

A dental beautification method is provided, wherein the user terminal function module implements the tooth beautification assisting method; and/or user terminal software; and/or user terminal applications.

A dental beautification method is provided, wherein the server function module is implementing the auxiliary method for tooth beautification; and/or server software; and/or server applications.

The invention also provides an auxiliary device for beautifying teeth, which comprises:

An acquisition module for acquiring information required for dental beautification;

An analysis module for performing data processing on the required information;

A generation module for generating a beautification scheme according to the data processing result.

The invention also provides a terminal device for dental beautification, which comprises a memory and a processor, wherein the memory is used for storing computer program codes, and the processor is used for executing the computer program codes stored in the memory to realize the tooth beautification auxiliary method.

Advantageous Effects of Invention (1) By setting up the user terminal, it is convenient to obtain the patient's oral cavity video, select teeth and display the beautification effect. It can also provide different treatment schemes for the patient to select and improve the patient's beautification enthusiasm. At the same time, the computing and storage functions are put on the server, which solves the shortcomings of insufficient computing capacity and storage space of the user terminal and gives full play to the advantages of convenient operation of the intelligent terminal.

(2) The system provides beautified tooth reference effects in advance, such as reference pictures and videos. Patients can participate in the design process, and the system can also provide different beautification schemes for selection, thus effectively improving the enthusiasm of patients for dental beautification.

BRIEF DESCRIPTION OF DRAWINGS

FIG. 7 is a CNN network structure of CNN cascade network Level 2 in the implementation method of the first way of implementation.

FIG. 8 is a schematic diagram of an implementation method of the second way of implementation.

DETAILED DESCRIPTION

Figure 1:
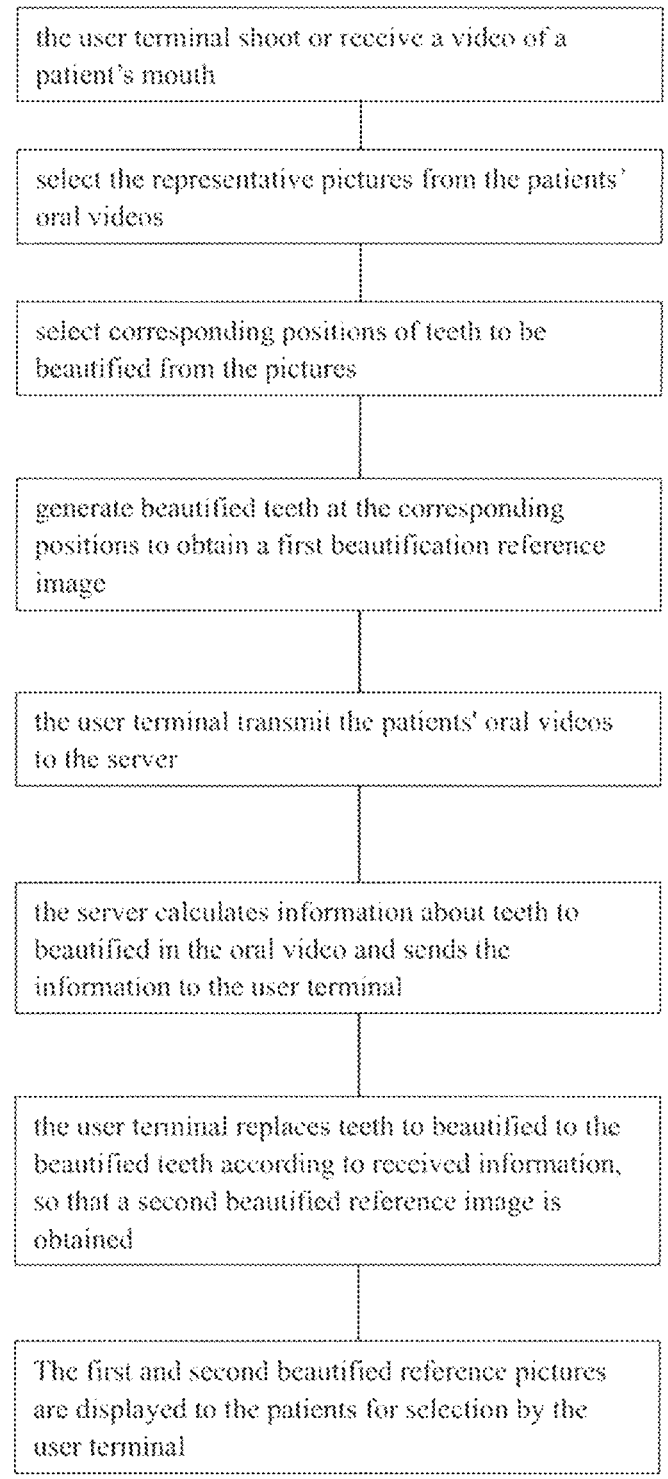
FIG. 1 is a schematic diagram of an implementation method of the first way of implementation.

As in the background of the invention, the dental beautification comprises tooth restoration, correction, whitening, tooth movement and other tooth cosmetic or plastic projects. As important organs of human body, teeth also affect people's faces to a great extent. For example, the faces with maxillary protrusion or mandibular protrusion change in a certain way after dental beautification. However, it is hard to test or estimate in advance what means to beautify the teeth in order to obtain a better surgical effect. Therefore, for a patient or a doctor, if the effect of tooth beautification can be seen in advance and intuitively, on the one hand, the doctor can determine the optimal operation plan in advance, on the other hand, the patient can know the effect after the operation in advance, and can negotiate the operation steps with the doctor in advance according to his own needs, which greatly improves the patient's experience and reduces the operation risk.

In addition, restoration, also called denture, is often used to protect the damaged tooth tissue or restore the missing tooth position for patients with tooth loss or defect. However, at present, the manufacture of dentures is generally not completed by doctors, but by factories specializing in the manufacture of dentures. Therefore, doctors and patients cannot know what state the prepared teeth will be in the future until the doctors receive the prepared dentures and the patient experience is poor.

According to the above situation, the present invention provides a C/S architecture-based dental beautification AR smart assistance method and corresponding devices and terminal equipment thereof, so as to help patients and doctors to visually and accurately see the beautified teeth in advance.

Wherein the user terminal refers to electronic products such as smart phones, tablet computers and personal computers, and the user terminal is provided with a camera. Specifically, the user terminal can start the camera according to user operation, and can also start the camera through the camera interface of the instant messaging application, such as starting the camera through the camera interface of the chat application.

The server shall be deemed to be construed as a service point providing process, database and communication facilities. For example, a server may refer to a single physical processor with related communication and data storage and database facilities, or may refer to a networked or clustered processor, a collection of related networks and storage devices, and operate software and one or more database systems and application software supporting services provided by the server. Servers can vary to a large extent in configuration or performance, but servers can generally comprise one or more central processing units and storage units. The server also comprises one or more large storage devices, one or more power supplies, one or more wired or wireless network components, one or more input/output components, one or more operating systems, such as Windows Server, Mac OS X, Unix, Linux, FreeBSD.

The specific technical scheme provided by the invention is detailed as follows:

I. An assisted dental beautification method comprises of the following specific steps:

(1) obtaining information required for dental beautification;

(2) processing the information, wherein the processing comprises at least one of analysis, calculation and matching, and obtaining an information processing result;

(3) generating a beautification scheme according to the information processing result;

(4) displaying beautified scheme.

The first dental beautification assistance method is illustrating in FIG. 1, wherein an AR intelligent assistance method for dental beautification based on C/S architecture is based on a user terminal and a server. Among them, C/S, that is, the structure of user terminal (also known as: Client, terminal equipment, etc.) and Server, can make full use of the advantages of the hardware environment at both ends, reasonably distribute tasks to the client side and the server side respectively, and reduce the communication overhead of the system. AR is short for Augmented Reality, which applies virtual information to the real world through computer technology. The first implementation creatively applies C/S and AR technologies to the field of dental beautification to help clients feel the visual effects of beautified teeth in advance.

Specifically, an auxiliary method of dental beautification utilizes a user terminal to communicate with a server, wherein the user terminal acquires oral information of a patient and analyzes, processes, and/or receives user instructions to generate a first beautified reference picture.

The user terminal transmits patient oral information to a server, which analyzes and processes the oral information and generates a second beautified reference picture.

The user terminal is utilized to respectively display the first beautified reference picture and the second beautified reference picture to the patient for selection.

The user terminal performs dental beautification assistance according to the following steps:

(A) the user terminal shooting or receiving videos of a patient's mouth.

(B) selecting the representative picture from the videos of the patient's mouth.

(C) selecting corresponding positions of teeth to be beautified from the representative picture;

(D) generating beautified teeth at the corresponding positions to obtain the first beautified reference picture.

The server performs dental beautification assistance according to the following steps:

(E) the user terminal transmitting the videos of the patient's mouth to the server, wherein the server calculates the information about teeth to be beautified in the videos and sends the information to the user terminal.

(F) the user terminal replacing teeth to be beautified to the beautified teeth according to received information, so that the second beautified reference picture is obtained;

The user terminal and the server can provide different beautified reference pictures respectively in the implementation method. The user terminal can quickly generate a beautified reference picture based on the patient's own teeth or data based on a database, and the patient can participate in the generation process of the beautified reference picture.

At the same time, the user terminal also transmits oral videos information to the server, which solves the shortcomings of the user terminal such as insufficient computing power and insufficient storage space, and can use strong computing power to calculate a more objective beautified reference picture, that is the second beautified reference picture.

The user terminal can simultaneously display a plurality of beautified reference pictures respectively generated by the user terminal and the server to the client, thereby effectively avoid that objective beautified reference pictures obtained by pure algorithms do not conform to the psychological expectation of patients and also avoid subjective errors and the like in beautified reference pictures generated by human participation. By using the invention, patients have short waiting time and strong participation feeling, and can select the most satisfactory and most suitable scheme from a plurality of beautified reference pictures; Effectively improve the enthusiasm of patients to beautify.

The specific steps of the implementation method are as follows:

(A) The user terminal or client terminal shoots or receives video of the patient's mouth.

The user terminal here can generally use smart terminal, such as smart phone and tablet computer. Now smart phones are very popular, with more and more portability and functionality, and are suitable as user terminals. At the same time, the oral cavity video of the patients can be transmitted to the user terminal after being photographed by professional cameras and other equipment, or can be directly photographed and acquired by the user terminal. In either case, when shooting the videos, the support and other tools should be used to assist to make the video recording better and more stable, reduce the influence of jitter blur and so on, so that the quality of the recorded video is higher, and the subsequent processing is more accurate.

(B) Select the representative picture from the video of the patient's mouth.

Figure 4:
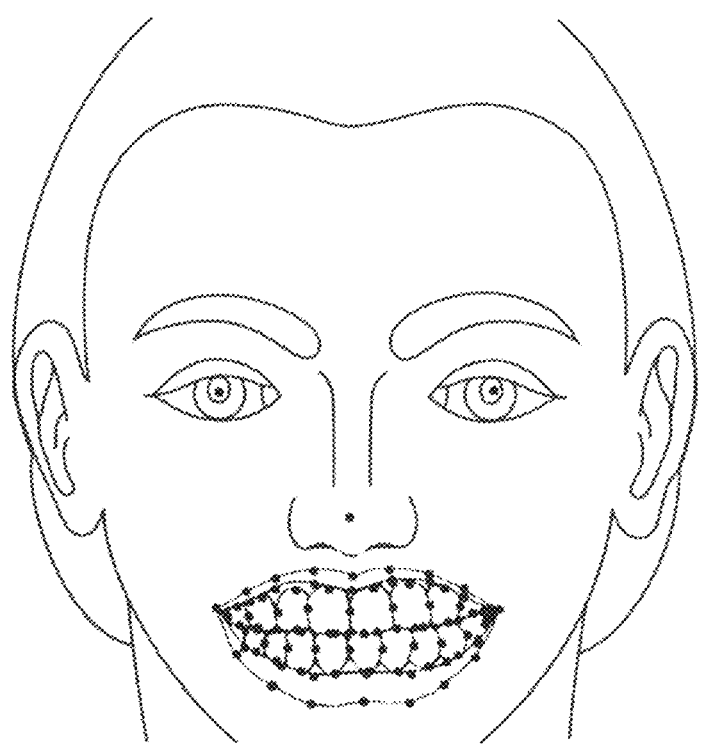
FIG. 4 is a schematic diagram of the positions of 83 key points to be detected in the implementation method of the first way of implementation.
Figure 5:
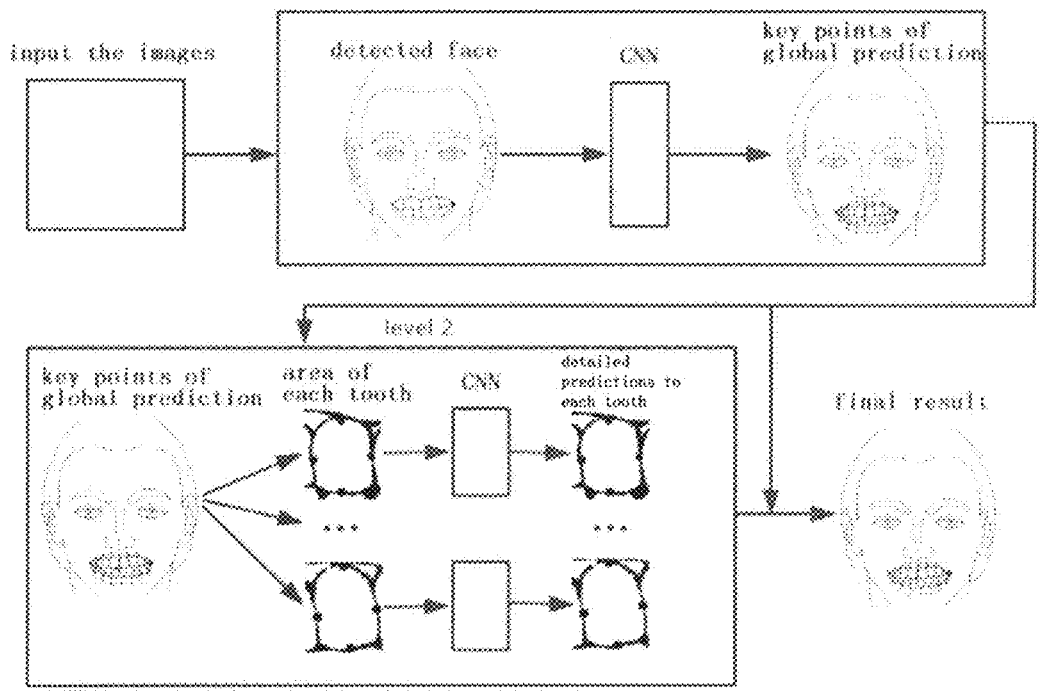
FIG. 5 is an overall architecture diagram of CNN cascade network in the implementation method of the first way of implementation.
Figure 6:
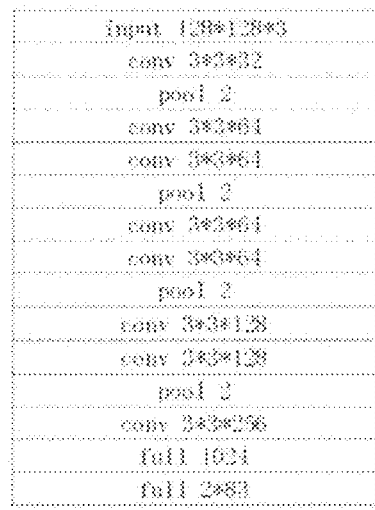
FIG. 6 is a CNN network structure of CNN cascade network Level 1 in the implementation method of the first way of implementation.

The front, left and right side pictures are selected simultaneously. Pictures can be selected automatically by the system or manually by doctors. As should be noted, the better the quality of the selected pictures are, the more accurate the subsequent teeth positions and color identification is. The pictures are effective information display diagrams of the patients, and the effective information comprises visible teeth, lips, eyes and nose under normal conditions in daily life, excluding cheeks and non-visible teeth under normal conditions. For convenience of display and operation, the present invention is illustrated in FIG. 4, taking a front view as an example.

When manually selected by doctors, on the one hand, the workload of doctors will be increased; on the other hand, due to subjective factors, it is not easy to select the picture with the best quality. Therefore, the system also provides automatic selection steps to reduce the workload of doctors and improve the objectivity of selection. When the required picture is automatically selected by the system, the following steps can be adopted:

(B1) Compare the human face of each frame picture with a standard human face model, and calculate the offset angle of the human face to obtain candidate pictures of the front, the left and the right sides.

(B2) Take out the oral cavity area in the candidate pictures, calculate the gray scale pictures, multiply the two gray scale differences in each pixel area of the gray scale pictures, and then accumulate pixel by pixel to calculate the score, with the formula to calculate is as follows:

$$D(f) = \Sigma_y \Sigma_x |f(x,y) - f(x+1,y)| * |f(x,y) - f(x,y+1)|;$$

Wherein, x and y represent the abscissa and ordinate of the pixel, respectively.

(B3) Select one of the front, left, and right pictures with the highest score from the candidate pictures to obtain the required representative picture.

The optimal way is: the system performs primary screening according to the above steps (B1) to (B3), and then the doctor performs secondary screening to finally determine representative picture.

(C) Select corresponding positions of teeth to be beautified from the picture.

This step is preferably decided after full communication between doctors and patients. First mark the teeth to be beautified, and then select the corresponding positions of the teeth to be beautified. The specific method for selecting the corresponding positions can be: using a rectangular frame to frame the teeth to be beautified, so that the rectangular frame just frames the teeth, i.e. the frame contains the length and width of the teeth to be beautified, so as to provide a basis for subsequent scaling of the teeth effect picture. When confirming the positions of teeth to be beautified such as framing teeth and determining symmetrical teeth, the selection can be made by means of computer algorithm or manually.

Figures 2, 3:
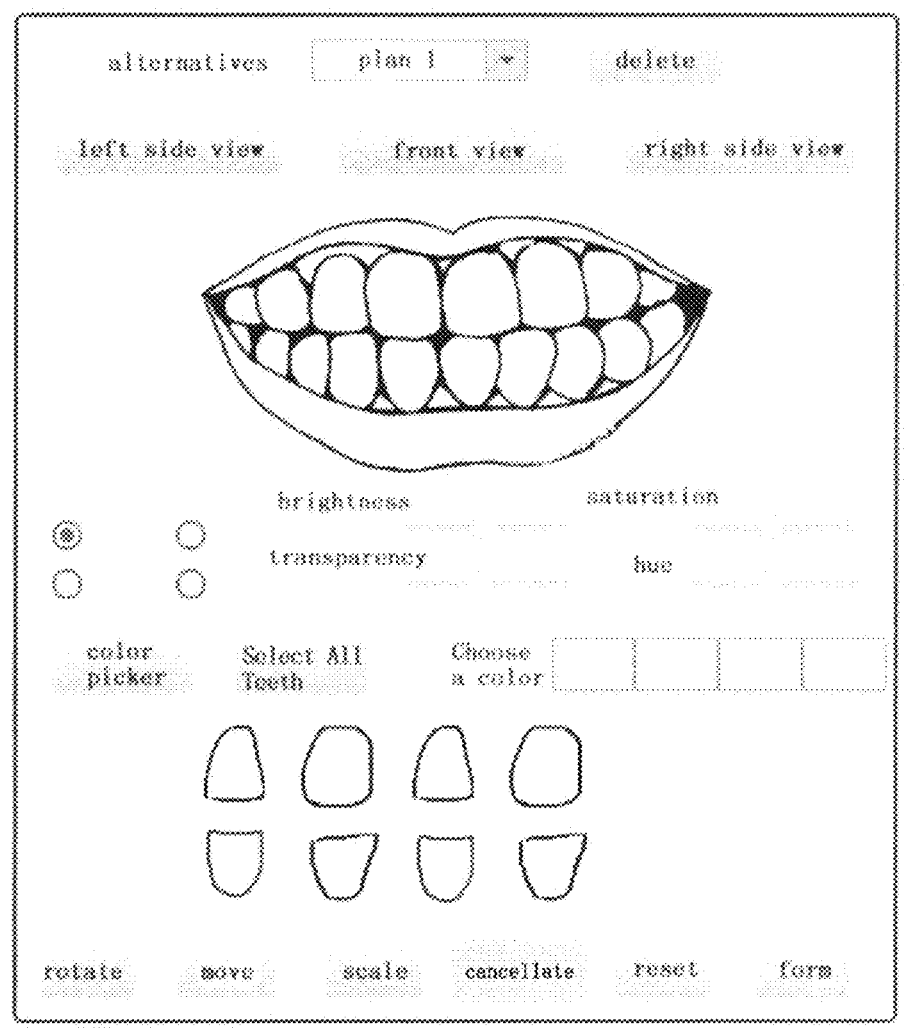
FIG. 2 is a schematic diagram of tooth numbers in the implementation method of the first way of implementation.
FIG. 3 is a schematic diagram of user terminal editing teeth in the implementation method of the first way of implementation.

As shown in FIG. 2, in order to confirm the positions of the teeth to be beautified and other required information in a more convenient way, the teeth positions may also be numbered in advance. The specific method of numbering is as follows: along the center line of the face to the outside, the right maxillary teeth are sequentially numbered 11, 12, 13 and 1m; The left maxillary teeth are sequentially numbered 21, 22, 23 . . . and 2m; The left mandibular teeth are numbered 31, 32, 33 . . . and 3m; The right mandibular teeth were numbered 41, 42, 43 . . . and 4m in sequence. Wherein m={1, 2, 3, 4, 5, 6, 7, 8}. The teeth 1m and 2m are symmetrical to each other, and the teeth 3m and 4m are symmetrical to each other. The teeth number data continues to be used in the step (specifically, step E) when the server processes teeth in the following method of the first way of implementation.

(D) Generate beautified teeth at corresponding positions in the picture to obtain the first beautified reference picture.

At present, there are a large number of various dental databases on the market, which can be selected/provided by companies/dental hospitals using this auxiliary method according to their needs. The database can be set in the background of the user terminal, can also be stored on the server, and can also be stored on other devices communicatively connected with the user terminal. After the teeth to be beautified are determined, the matching teeth model can be directly selected from the teeth database and the teeth to be beautified in the picture can be replaced. But if all the teeth to be beautified are operated as above, the data processing capacity will increase; And there will be certain differences between the even perfect teeth model and the patients' own teeth.

Therefore, it is better to treat each tooth to be beautified according to the following steps in this step:

(D1) Judge whether the teeth symmetrical to the teeth to be beautified need to be beautified. If the symmetrical teeth do not need to be beautified, executing steps D2 to D4, or executing steps D2 to D8. If the symmetrical teeth need to be beautified, steps D5 to D8 are directly executed.

(D2) Calculate the width and height of the teeth to be beautified, and cut the teeth symmetrical to the teeth to be beautified according to the contour to obtain replacement teeth picture.

(D3) Turn over a horizontal mirror picture of the replacement teeth picture and perform scaling processing, wherein the width and height of the scaled replacement teeth picture is consistent with the width and height of the teeth to be beautified.

(D4) Paste the scaled replacement teeth picture on the corresponding position of the picture in step C to obtain first beautified reference picture I.

(D5) Select candidate teeth models from the teeth model base according to the comprehensive information of the patients' age, gender, teeth corresponding positions, etc.

(D6) Select the replacement teeth model with the closest color from the candidate teeth models according to the adjacent unselected teeth colors.

(D7) Calculate the width and height of the teeth to be beautified, and scale the teeth picture of the front angle of the replacement teeth model to the same width and height as the width and height of the teeth to be beautified.

(D8) Paste the scaled teeth picture to the corresponding positions of the teeth to be beautified in the three representative pictures in step C to obtain first beautified reference picture II.

As should be understood is that the actual meaning of the above steps is: if the symmetrical teeth of the teeth to be beautified do not need beautification, it's acceptable that only obtain the first beautified reference picture I, and surely can also obtain both the first beautified reference picture I and the first beautified reference picture II simultaneously. If the symmetrical teeth also need beautification, the first beautified reference picture II is a must. In practical operation, reasonable step selection is carried out according to the patients' situation, so that the patients can obtain more options and save operation steps.

FIG. 3 illustrates an interface for editing teeth to be beautified on a user terminal in the first implementation method. FIG. 3 illustrates a front view, which can also be switched to other pictures by clicking the corresponding button. At the same time, the interface adds editing function, which can adjust the colors of teeth by modifying hue, saturation, brightness, transparency, etc. You can also adjust the colors of the whole teeth or some part of the teeth by selecting "Select All, Neck, Middle, Cut" etc. The colors of the adjacent teeth which don't need to be beautified on the picture can be retrieved by the color picker as the colors of the teeth to be beautified. And several tooth colors can also be preset for selection. You can also edit all teeth through the "Select All Teeth" button, such as uniformly adjusting the color and positions of all teeth. It is also possible to select different tooth models for teeth with different numbers, or to select different tooth models for teeth with the same number in different schemes. You can also adjust the teeth shape by clicking the shape button. The interface also includes functions of rotation, movement, scaling, cancellation, reset, etc. As should be understood is that the interface shown in FIG. 3 is only one of the implementations. In practical operation, editing functions can be selected, increased or decreased as needed.

Under the condition of full communication and joint participation between the patient and the doctor, the first beautified reference picture is first generated on the client using steps A to D for the patient's reference. In this way, the patient has a short waiting time and a strong sense of participation, which can enhance user experience. While performing steps A to D, the oral information (oral videos) obtained in step A is transmitted to the server, and steps E to F are jointly performed on the server and the client to generate the second beautified reference picture, which is more objective. Because the server needs a certain time for data analysis and processing, using this time to simultaneously perform steps A to D can also reduce the waiting time for customers (patients) to have nothing to do and further enhance the user experience.

Steps E to F are as follows:

(E) The user terminal transmits the patients' oral cavity video to the server, and the server calculates the position information and color information of the teeth to be beautified in the patients' oral cavity video and sends the information to the user terminal.

As illustrated in FIG. 4 to FIG. 7, in the step E, the server calculates the position information of the teeth to be beautified by the following steps:

(E1) Decode the oral video of the patients to obtain key frame images and non-key frame images.

(E2) For key frame images, the cascade convolutional neural network CNN is used to locate the coordinates of key points and calculate the teeth positions.

(E3) For non-key frame images, Lucas-Kanade sparse optical flow algorithm is used to calculate the teeth positions according to the coordinates of key points. The teeth positions herein the video is calculated by the algorithm combining key points detection and tracking. The cascade convolutional neural network CNN is used for key points detection and Lucas-Kanade sparse optical flow algorithm is used for key points tracking. Because the key points detection is time consuming, the preferred scheme is to detect the key points only in the key frames of the videos, and using sparse optical flow algorithm for the non-key frames to point track to improve the processing speed.

The step E2 comprises the following steps:

(E21) Face detection is carried out on the key frame images, and the face detector based on Haar features carried by OpenCV vision library is used for detection, and the detected face images are intercepted and normalized to 128*128 size.

(E22) Set the CNN network of Level 1 to be 128 in width, 128 in height and 3 in image channel. An activation layer is behind each convolution layer in the CNN network. The activation layer uses Sigmoid function as the active function, and the last two layers are full connection layers.

(E23) The normalized face images in step E21 are used as CNN network input of Level 1. The output of Level 1 is 83 key points of global prediction. The attributes of each key point are X and Y coordinate values and whether it is occluded or not. As shown in FIG. 4, 83 key points include 50 teeth, 30 lips, 1 nose and 2 eyes. The coordinates of 50 key points of teeth are selected from the 16 teeth numbered 11 to 14, 21 to 24, 31 to 34, 41 to 44 in the step C. The 16 teeth are daily visible teeth. Due to the relative coordinate relationship between the key point positions of teeth and the key point positions of eyes, nose and lip, 83 key point coordinates were finally selected from CNN.

(E24) For the 16 teeth, an image with a size of 18*18 pixels is taken from each tooth as the center as the CNN network input of Level 2, and the CNN network output of Level 2 re-predicts 4 key points around each tooth to obtain coordinate values of 50 key points around the fine-tuned 16 teeth, wherein adjacent teeth share one key point left and right, and the coordinate values of the shared key points take the average value of the two teeth predictions.

(E25) The numbers of 4 key points around the teeth to be beautified are determined according to the numbers of the teeth to be beautified.

(E26) Four key point coordinates around the teeth to be beautified are obtained according to the 50 key point coordinate values.

(E27) Obtain the position information of the teeth to be beautified in the key frames according to the coordinates of four key points around the teeth. Both Level 1 and Level 2 select L2 Loss as the loss function and sum the square difference. The formula is as follows: $L=\Sigma_{i=0}^{N-1}\|Y_i - f(X_i)\|_2^2$, wherein f represents the calculation result of CNN, N represents the number of coordinates to be predicted by the network, $X_i$ is the input of the network, $Y_i$ is the correct coordinate value marked by the training sample, and i represents the number of frames.

In the step E3, two adjacent key frames are set as the $j^{th}$ frame and the $i+k^{th}$ frame, and non-key frames between the two adjacent key frames are tracked according to the following steps:

(E31) The tracking method for the non-key frames $i+1^{th}$ to $i+k/2^{th}$ frames comprises the following steps: selecting the $i^{th}$ frame as the first frame to initialize, predicting the position of the $i+1^{th}$ frame with the position of the $i^{th}$ frame, predicting the position of the $i+2^{th}$ frame with the position of the $i+1^{th}$ frame, and so on, tracking to the $i+k/2^{th}$ frame.

(E32) The tracking method for the non-key frames $i+k/2+1^{th}$ to $i+k-1^{th}$ is to select the $i+k^{th}$ frame as the first frame for initialization, predicting the position of the $i+k-1^{th}$ frame with the position of the $i+k^{th}$ frame, predicting the position of the $i+k-2^{th}$ frame with the position of the $i+k-1^{th}$ frame, and so on, and tracking to the $i+k/2+1^{th}$ frame. It should be understood that the tracking method for the non-key frames is to select two adjacent key frames as the first frame respectively and track the positions of the non-key frames from both ends to the middle. For the non-key frame images, only 4 key points around the teeth to be beautified need to be tracked, while the other key points around the teeth, lip and nose are not tracked.

Since jitter may occur when the non-key frames are tracked by optical flow, in order to avoid this situation, a better scheme is to smooth the tracked non-key frame positions by curve quadratic fitting. As in step E3, each key point in the non-key frame image is smoothed according to the following steps:

(E33) For any key point, select the quadratic equation $$f(z) = b_0 + b_1 z + b_2 z^2.$$

(E34) The values of two adjacent key frames and all non-key frames between the two adjacent key frames are brought into the quadratic equation, $(h, d_h)$, $h \in [0,H]$, wherein H is the sum of the two key frames plus the number of non-key frames between the two key frames, renumbering the key frames and all non-key frames between the two key frames by taken smaller index values in the two key frames as the $0^{th}$ frame, h is the renumbered the $h^{th}$ frame, and $d_h$ is the coordinate value of the key point in the $h^{th}$ frame.

(E35) Define a loss function:

$$Q = \Sigma_h (f(Z) - b_0 - b_1 z - b_2 z^2), h \in [0,H], \text{ respectively}$$

bringing an abscissa z value and an ordinate f(z) value into the loss function Q, so to obtain the value of $b_0$, $b_1$, and $b_2$ respectively, which minimize the value of Q, to obtain two different curve equations.

(E36) Respectively bringing h into the two curve equations, and the smoothed coordinate values of the key points in the non-key frames are calculated.

There are many ways to calculate the colors of replacement teeth at the server. The implementation method is provided by the invention, wherein the color change of the replacement teeth is calculated by calculating the overall color change trend of all the tooth areas, that is, the step E includes: (E4) Calculate the color information of the teeth to be beautified. The step E4 includes:

(E41) Intercept the entire teeth area in each frame according to the 50 key point coordinate values.

(E42) Select the LAB space and calculate the average of all pixels in the whole teeth area under the L, A, B channels respectively, to obtain (La_i, Aa_i, Ba_i), wherein a represents the whole teeth region, i represents the $i^{th}$ frame.

(E43) Based on the LAB value (La_front, Aa_front, Ba_front) of the front view, calculate the change value of each channel in each frame forward and backward respectively according to the following formula:

$$\begin{cases} \text{La\_sub} = (\text{La\_i} - \text{La\_front})/\text{La\_front}; \\ \text{Aa\_sub} = (\text{Aa\_i} - \text{Aa\_front})/\text{Aa\_front}; \\ \text{Ba\_sub} = (\text{Ba\_i} - \text{Ba\_front})/\text{Ba\_front}; \end{cases}$$

(E44) Calculate the LAB channel color value of the $j^{th}$ pixel point of the teeth to be beautified in the $i^{th}$ frame image according to the following formula:

$$\begin{cases} \text{Lj\_i} = \text{Lj\_front} + \text{Lj\_front} * \text{La\_sub}; \\ \text{Aj\_i} = \text{Aj\_front} + \text{Aj\_front} * \text{Aa\_sub}; \\ \text{Bj\_i} = \text{Bj\_front} + \text{Bj\_front} * \text{Ba\_sub}. \end{cases}$$

Through the above steps, more accurate tooth color information can be obtained.

(F) The user terminal replacing teeth to be beautified to the beautified teeth according to received information, so that the second beautified reference picture is obtained;

Through the above steps A to D performed at the client and steps E to F performed jointly at the server and the client, relatively subjective first beautified reference picture and relatively objective second beautified reference picture are respectively obtained. Next, step G is carried out.

(G) The first and second beautified reference pictures are displayed to the patients for selection by the user terminal.

Preferably, the invention can also display the beautification reference effect video to the patients for reference. That is, on the basis of the above steps, the original oral cavity video of the patients is processed, the teeth to be corrected/beautified in the video are replaced with beautified teeth, and then are dynamically displayed, so as to further improve the display accuracy.

The method of the invention also provides a second embodiment, which differs from the first embodiment mainly in that the embodiment simulates the patient's face model through various parameters obtained, and also refers to the face fitting when generating the final treatment scheme. In addition, when the scheme is generated in this embodiment, the surgical instrument scheme needed for the treatment is also generated, which has been referred to during the treatment.

As shown in FIG. 8, the specific steps of this mode of implementation are as follows:

Step S110: get multiple parameter data.

The multi-parameter data included CT image data of the patient's teeth, intraoral model data, and multiple images of the patient's face from different angles. Among them, Computed Tomography (CT) was used to scan the teeth of the patient to obtain the CT image data of the patient's teeth, including alveolar bone image, root image and other information. The oral cavity of the patient was scanned by the intraoral scanner to obtain the intraoral model data of the patient, including images of tooth crowns and gums visible to the naked eye. Images of the patient's face from different angles were collected by camera, so as to generate the patient's face model based on the multiple face images.

Step S120 establishes the user's face model according to the multiple parameter data.

In other words, the user's face model was established based on the CT image data of the patient's teeth, the model data of the patient's mouth and the data of the patient's face from different angles. Specifically, the CT image data of the tooth are structures invisible to the naked eye in the patient's mouth, such as alveolar bone and tooth root, but these structures can be presented under CT scanning. The intraoral model data are structures visible to the naked eye in the patient's oral cavity, such as the dental crown, etc. Therefore, the intraoral model data can be displayed in coincidence with the CT image data of the teeth. Due to the model data in the mouth and teeth CT image data with different size, the model data to facilitate the mouth can overlap with dental CT image data and model data adjusted respectively the mouth of predetermined size and adjust the dental CT image data for another book size, makes the model data within the mouth of the patients with CT image data can coincides with teeth.

In addition, it is necessary to adjust the size of the patient's face data from different angles, and generate the face model based on the adjusted size of the face data. The model data in the mouth and the tooth CT image data are displayed at the corresponding positions of the face model. Therefore, the user can see the model data, tooth CT image data and the overall face of the patient through the face model.

In step S130, the anatomical structure of the tooth part of the face model is analyzed to obtain the analysis result.

Because of the dental beautification, the anatomical structure of the tooth part of the facial model is analyzed, and the anatomical structure of the tooth part includes the data of tooth root, neural tube, bone density and so on. Since there is a lot involved in tooth beautification, it is necessary to analyze the influence of various anatomical structures, so as to facilitate the follow-up treatment. If this tooth is moved to the right, the position of the corresponding tooth root will change. Thus, the results of this analysis are the correlations between the teeth.

Step S140 simulates a variety of treatment regimens based on the analysis results and presents the dental and facial changes of the facial model in real time.

The multiple treatment schemes are designed for doctors according to the needs of patients. In other words, doctors can try different treatment schemes on the face model according to the correlation between the teeth. The treatment effect of different treatment schemes will be presented to patients in two or three dimensions on the terminal device in real time. The treatment effect is specific to the tooth changes in the face model and the overall facial changes caused by the tooth changes when doctors apply different treatment regimens to the face model. Therefore, before receiving treatment, the patient can know in advance the therapeutic effect that will be obtained if the treatment regimen is adopted. In particular, the facial model can also show the changes of the whole face after beautification of the teeth. For patients with orthodontic or buck teeth, the facial changes after orthodontic can be visually seen to improve the user's experience.

Step S150: select the treatment scheme with the best therapeutic effect presented in the various treatment schemes as the final treatment scheme.

Since the doctor has simulated a variety of treatment options on the face model, the best treatment option presented in the treatment options is selected as the final treatment option. The best judgment of the treatment effect was that when the treatment scheme was applied to the face model, the teeth of the face model were arranged neatly and the whole face presented a better effect. Easy to understand, doctors and patients can determine the final treatment plan based on the simulation effect.

After the final treatment plan is determined, multiple surgical instruments needed in the treatment process will be customized according to the final treatment plan. It should be noted that since orthodontics involves multiple steps, and the surgical instruments required for each step are different, multiple virtual surgical instruments can be customized according to each link of the final treatment plan, so as to facilitate the processing of the virtual surgical instruments for actual treatment.

Thus, it can be seen that the embodiment of the invention provides a dental beautification simulation method to establish a face model of the patient through multiple parameters of the patient itself, and simulates a variety of treatment schemes on the face model to determine the final treatment scheme. During the simulation, both the patient and the doctor can directly see the therapeutic effect brought by the treatment plan, which includes changes in teeth and overall facial changes to improve the user's experience.

The invention also provides a third embodiment, which also adds a step to judge whether the information meets the preset conditions in terms of data processing to further improve the rationality of the generation scheme.

Figure 9:
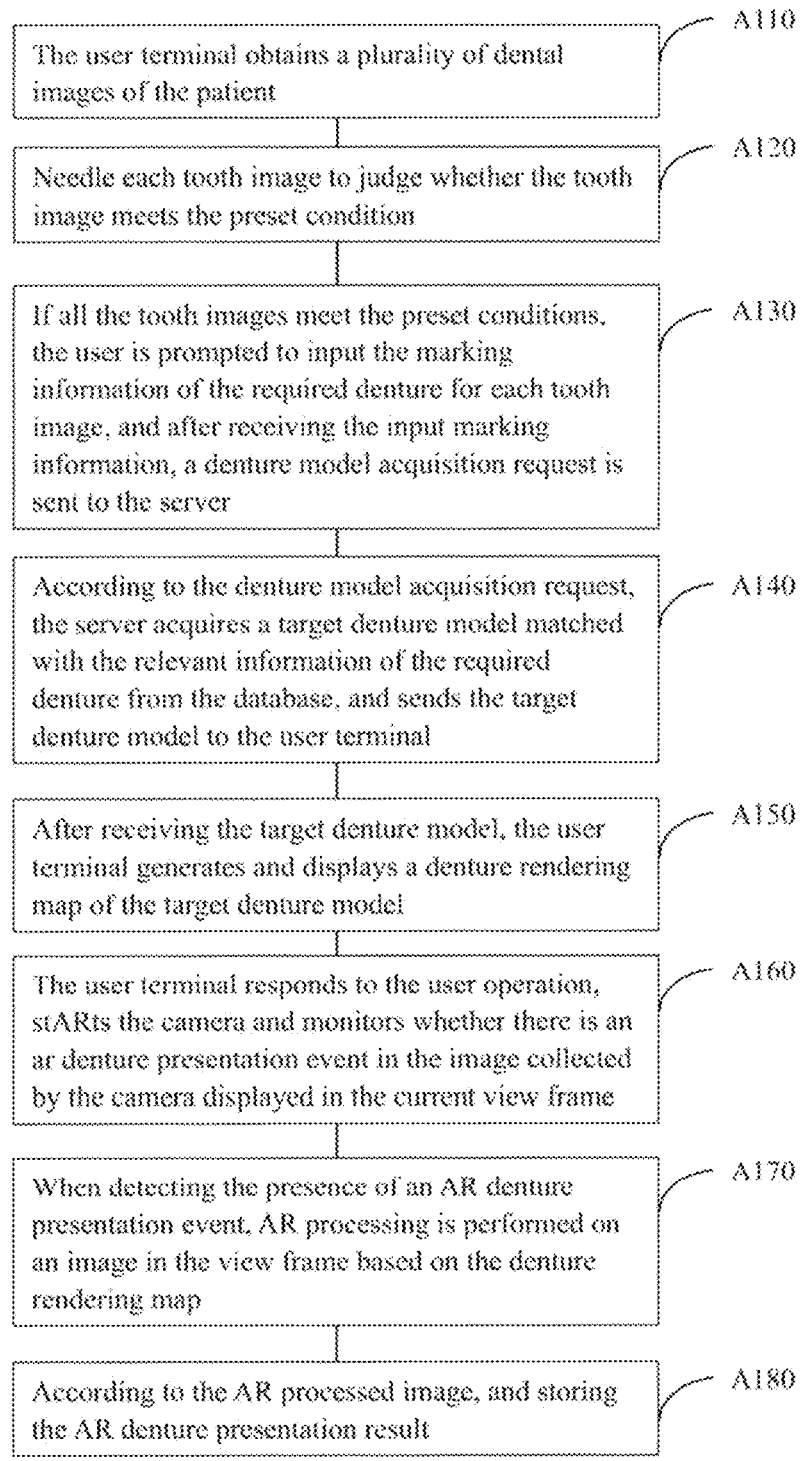
FIG. 9 is a schematic diagram of an implementation method of the third way of implementation.

This embodiment is based on the communication between the user terminal and the server. As shown in FIG. 9, the specific process of this implementation is as follows:

Step A110, the user terminal obtains multiple dental images of the patient.

Different tooth images correspond to different shooting angles. Each tooth image can be obtained directly from the image of the library in advance, or directly obtained by receiving tooth images from an external terminal, or can also be a doctor or as a consultant in communication with patients, as described in the user terminal through a response to a doctor or a consultant operation, start the camera under different angle (typically at least three angles, tooth positive angle and the characteristics of regional characteristics of the area of the two side view) described in the patient's teeth images, such as described in the teeth of the image acquisition can undertake choosing according to the actual situation. A better approach is to try to position the patient in a characteristic position (such as a smile position) during the process of taking a picture of the patient's teeth, so that the image of the teeth can more easily meet the preset conditions.

Step A120, for each tooth image, determine whether the tooth image meets the preset conditions.

The user terminal conducts image analysis for each tooth image to determine whether the tooth image includes a tooth feature area. When the judgment result is, that is, the tooth image includes a tooth feature area, the tooth image meets the preset conditions. Accordingly, if the judgment result is no, that is, the tooth image does not include the characteristic area of the tooth, then the tooth image does not meet the preset conditions.

It is worth noting that if the tooth image does not meet the preset conditions, the user is prompted to re-shoot the tooth image at the corresponding angle, and continue to determine whether the reshot tooth image meets the preset conditions until the reshot tooth image meets the preset conditions.

Step A130: if all the tooth images meet the preset conditions, the user is prompted to input the label information of the required denture for each tooth image, and after receiving the input label information, a request for obtaining the denture model is sent to the server.

In this embodiment, if all dental images meet the preset conditions, that is, all dental images include dental feature areas, then the user terminal prompts the user to input the required denture labeling information for each dental image, and the user can input the required denture labeling information according to the actual situation of the patient. Wherein, the labeling information includes the position information of the required denture, that is, the tooth area of the required denture. The user terminal sends the denture model acquisition request to the server after receiving the input annotation information. Specifically, the denture model acquisition request includes the required denture association information, which includes the patient information, each tooth image, and the labeling information for each tooth image.

Worth mentioning is that described patient information can be obtained from a pre-stored patient information database. In case the patient information is not stored in the pre-stored patient information database, a doctor can input the patient information before taking the patient's tooth image. Among them, the patient information includes the information such as name, gender, and age of the patient.

In step A140, the server obtains the request according to the denture model, obtains the target denture model matching the required denture association information from the database, and sends the target denture model to the user terminal.

In this embodiment, the server includes a database that stores a plurality of denture models and the associated information for each denture model, including the gender, age, shape parameters and other information of the corresponding denture model. Server first described in denture model after get request received stated, described the denture model get request parsing, obtain the needed information associated with a false teeth, and then, the required information associated with a false teeth and described each denture model of correlation information in the database matching and obtain the needed information associated with a false teeth and described each denture model of correlation information in the database matching degree between, lastly, matching degree is the highest dentures model as the target model, and will be described in the denture model is sent to the user terminal.

It is worth noting that the target denture model is not limited to one, the number of which is related to the number of required dentures. For example, the required denture is two front teeth, then the target denture model is the denture model with the highest matching degree with the two front teeth respectively.

Step A150, after the user terminal receives the target denture model, generates and displays the denture rendering of the target denture model.

In the user terminal after the denture model is received, the user can adjust the denture model by an operation such as scaling, then the user can choose according to the patient's needs corresponding denture rendering parameters, and then based on the user's choice of dentures to generate and render parameters according to stated goals dentures model rendering, among them, the described denture rendering parameters including false color and material parameters.

In conclusion, the implementation way uses the server to interact with the user terminal, and can be more efficient to generate and display target denture model rendering, within a few minutes to complete the entire process, provide the patient with a multi-angle view before receiving dentures, rendering a realistic 3-dimensional view, visualization degree is higher, and can effectively improve the patient's clinic experience. In addition, as most of the work is done by the user terminal and server, the user's professional requirements are reduced, reducing the error caused by human operation.

Further, on the basis of the above, in order to make the patient more intuitive to see the effect after dental beautification, the dental beautification effect generation method can also include the following steps:

In step A160, the user terminal responds to the user operation, starts the camera and monitors whether there is an AR denture rendering event in the image displayed in the current viewfinder box collected by the camera.

Specifically, the user terminal can control the camera to be in the AR shooting mode according to the user's operation. For example, when the user selects the AR shooting option, the camera can be in the AR shooting mode. Described in the process of camera, the user terminal in the viewfinder display through the image obtained by camera, monitor to photograph the event, the AR using image recognition technology to display in the frame of image recognition, determine the mentioned in the viewfinder display through the camera whether collected images for face image, if the face image, then identify whether mentioned in the face image contains characteristics posture, if contain features posture, events will determine AR dentures as monitoring to exist.

Step A170, when the presence of AR denture rendering event is detected, AR processing is performed on the image in the viewfinder box based on the rendering image of the denture.

When the user terminal monitors an AR denture presentation event, first determine described the characteristics of the image contains posture image region, and then based on the above dentures rendering to AR the described characteristics pose image region, described the dentures rendering shows it is described in the image characteristics of the position corresponding to the location of the image area.

Step A180 shows the AR denture rendering result according to the image processed by AR, and stores the AR denture rendering result.

When the user terminal displays the results of the AR denture according to the AR processed image, the patient can visually view the effect after the beautification of his teeth. Through the application of AR augmented reality technology, the rendered image of the denture is locked on the dental arch, and the face movement is tracked in real time, so as to achieve better results. In addition, during the presentation process, the results of AR denture presentation were also stored in the form of video or two-dimensional map, and exported to the denture factory that made the teeth, so as to help them refer to the shape and color during the production process.

Figure 10:
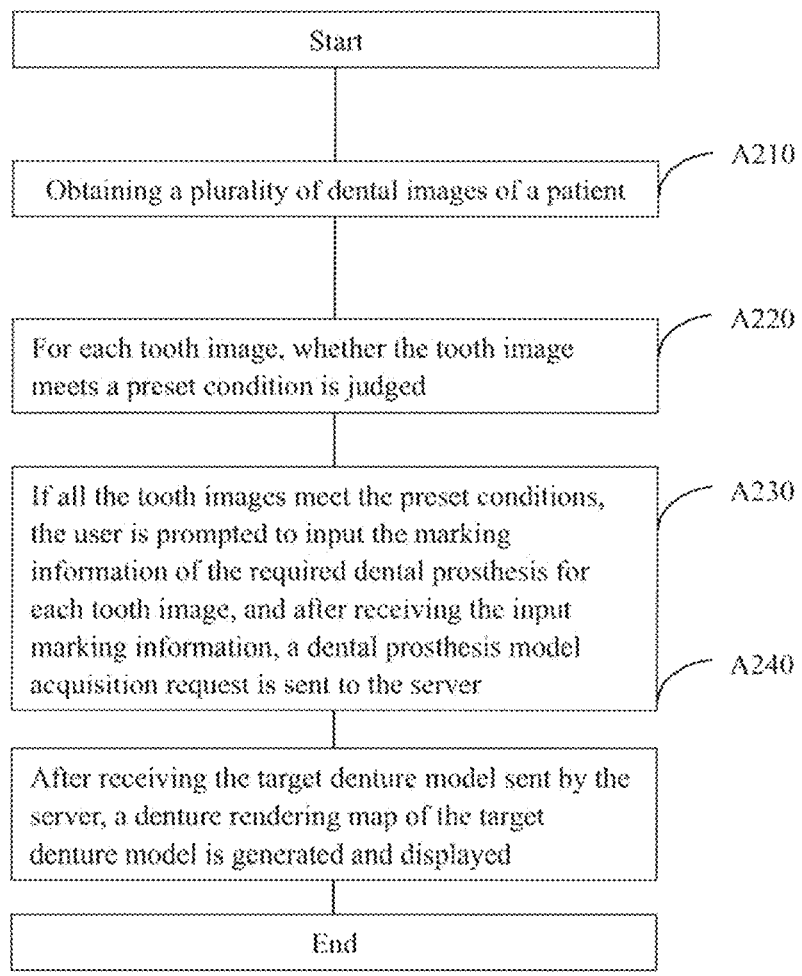
FIG. 10 is a schematic diagram of optimization method of an implementation method of the third way of implementation.

Further, as shown in FIG. 10, the invention also provides an optimal solution for the method described in FIG. 9. The scheme is executed by the user terminal. The steps involved in the method to be described next have been described in the illustration of the method in FIG. 9 above. Detailed details of each step can be referred to the description of the embodiment above.

Step A210 is used to obtain multiple dental images of the patient, in which different dental images were taken from different angles.

Step A220, for each tooth image, determine whether the tooth image meets the preset conditions.

Step A230: if all the tooth images meet the preset conditions, the user is prompted to input the label information of the required denture for each tooth image, and after receiving the input label information, a request for obtaining the denture model is sent to the server.

The server obtains the request from the database to obtain the target denture model matching the associated information of the required denture from the denture model according to the denture model request. Wherein, the acquisition request of the denture model includes the associated information of the required denture, which includes the patient information, the image of each tooth and the label information of each tooth image.

Step A240, after receiving the target denture model sent by the server, generates and displays the denture rendering of the target denture model.

The rest of the steps follow an illustration of the method in FIG. 9.

II. An auxiliary device for dental beautification, including the following functional modules:

Acquisition module for obtaining information needed for dental beautification;

Analysis module for data processing of required information;

The generation module is used to generate the beautification scheme according to the result of data processing.

Figure 11:
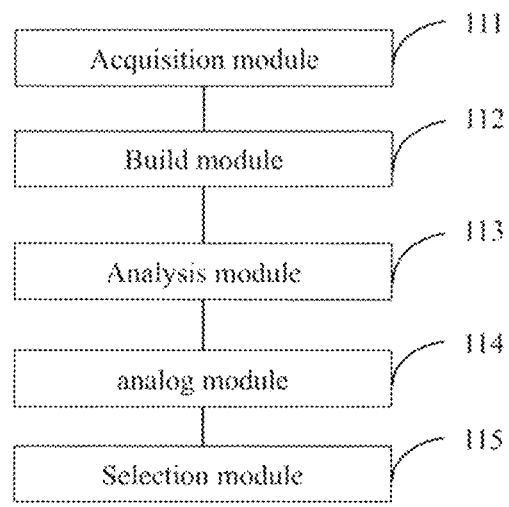
FIG. 11 is a schematic diagram of the device provided by the first way of implementation.

An embodiment of the device is shown in FIG. 11, which includes obtaining module 111, establishing module 112, analyzing module 113, simulating module 114 and selecting module 115. The implementation of the device can correspond to the second implementation of the dental beautification auxiliary method mentioned above (see FIG. 8). The corresponding relationship of specific implementation is as follows:

Obtaining module 111 is used to obtain multiple parameter data. Step S110 can be performed by obtaining module 111.

Establishing module 112 is used to build the user's face model based on multiple parameter data. Step S120 can be performed by establishing module 112.

The analysis module 113 is used to analyze the anatomical structure of the tooth part of the facial model to obtain the analysis results. Step S130 can be performed by the analysis module 113.

The simulation module 114 is used to simulate a variety of treatment regimens based on the analysis results and to present tooth changes and facial changes of the facial model in real time. Step S140 can be performed by the simulation module 114.

A selection module 115 is selected to select the treatment scheme with the best therapeutic effect among the various treatment schemes as the final treatment scheme. Step S150 can be performed by the selection module 150.

Figure 12:
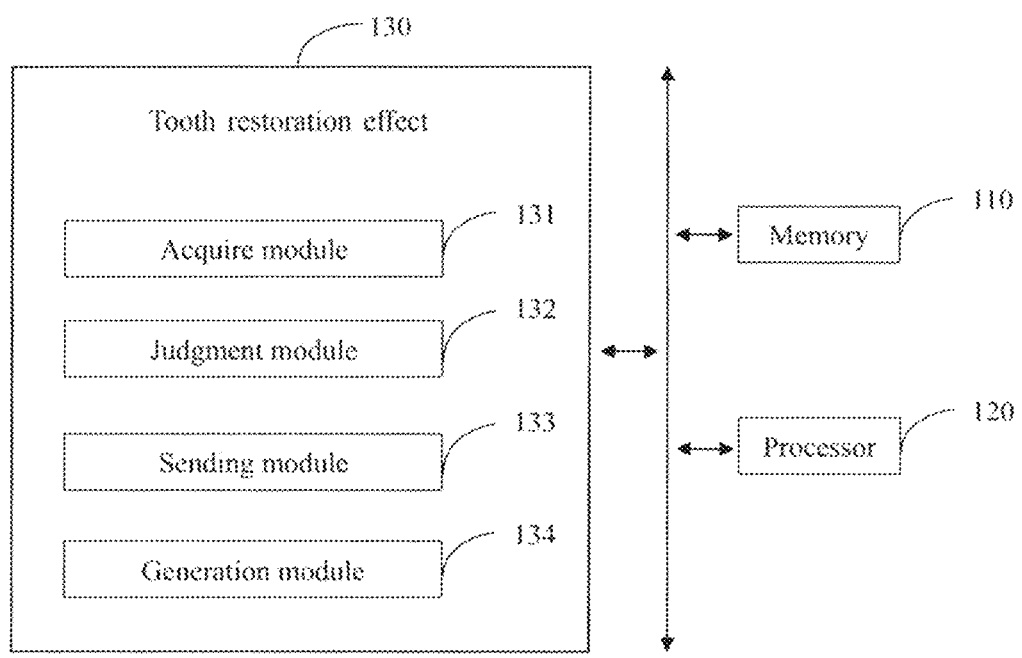
FIG. 12 is a second schematic diagram of the device provided by the second way of implementation.

Another embodiment of the device is shown in FIG. 12. The user terminal comprises a tooth beautification effect generation device 130, a memory 110 and a processor 120. The implementation mode of this device can correspond to the third implementation mode of the auxiliary method of dental beautification mentioned above (see FIGS. 9 and 10).

The tooth beautification effect generating device 130 comprises at least one software functional module that can be stored in the memory 110 in the form of software or Firmware or solidified in the Operating System (OS) of the user terminal. The processor 120 is used to execute the executable software modules stored in the memory 110, for example, the software function modules and computer programs included in the tooth beautification effect generation device 130. In this embodiment, the tooth beautification effect generation device 130 may also be integrated into the operating system as part of the operating system. Specifically, the tooth beautification effect generation device 130 includes:

The obtaining module 131 is configured to obtain multiple dental images of the patient, in which different dental images were taken from different angles.

Judgment module 132 is used to judge whether the tooth image meets the preset conditions for each tooth image.

Delivery module 133, for if all teeth images meet preset conditions, will prompt the user for each teeth image enter the required labelling information, false and after receives the input labelling information, the server sends to the stated denture model get request, in order to server according to the above stated denture model described get request from the database access to match the required information associated with a false teeth denture model, which described denture model to obtain the related information, including a need false teeth in the request described the correlation information including patient information, each tooth image and each tooth of the image information.

Generation module 134 is used to generate and display a denture rendering of the target denture model after receiving the target denture model sent by the server.

Further, the embodiment also provides a readable storage medium in which a computer program is stored and the computer program is run to achieve the tooth beautification effect generation method.

III. An Auxiliary Terminal Device for Dental Beautification.

Figure 13:
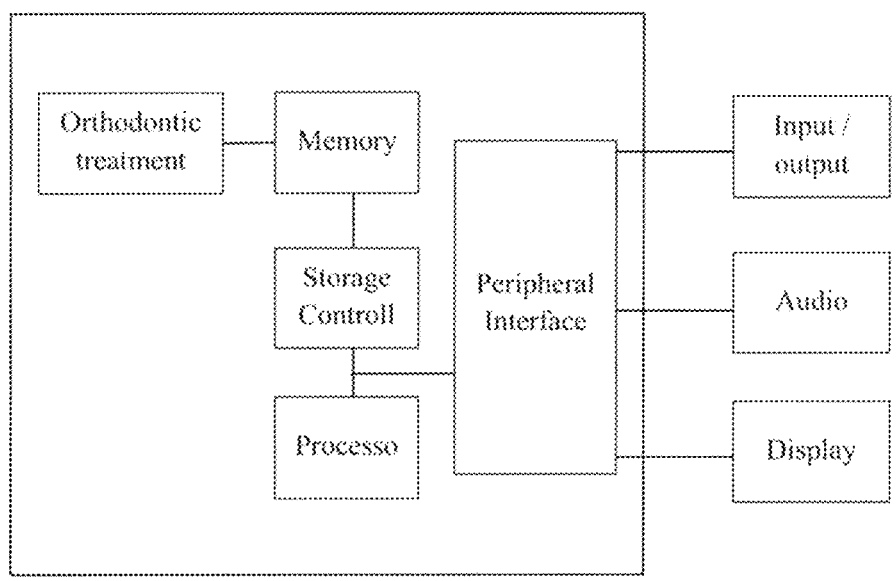
FIG. 13 is a schematic diagram of the terminal device provided by the first way of implementation.

As illustrated in FIG. 13, it is a schematic structural diagram of a terminal device provided by an embodiment of the present invention. The user terminal comprises a dental beautification simulation device (orthodontic treatment simulation device), a memory, a storage controller, a processor, a peripheral interface, an input/output unit, an audio unit, and a display unit.

Each element of the memory, the storage controller, the processor, the peripheral interface, the input/output unit, the audio unit and the display unit are directly or indirectly electrically connected with each other to realize data transmission or interaction. For example, these elements can be electrically connected to each other through one or more communication buses or signal lines. The dental beautification simulation device comprises at least one software function module which can be stored in the memory or solidified in an operating system (OS) of a user terminal in the form of software or firmware. The processor is used for executing an executable module stored in a memory, such as a software function module or a computer program included in the dental beautification simulation device.

The memory may be, but is not limited to, Random Access Memory (RAM), Read Only Memory (ROM), Programmable Read-Only Memory (PROM), Erasable programmable read-only memory (EPROM), electrically erasable programmable read-only memory (EEPROM), etc.

The memory is used for storing a program, and the processor executes the program after receiving an execution instruction. The method executed by the user terminal defined by the flow process disclosed in any one of the embodiments of the present invention can be applied to or implemented by the processor.

The processor may be an integrated circuit chip with signal processing capability. The processor may be a general-purpose processor, such as Central Processing Unit (CPU), Network Processor (NP), etc. It may also be digital signal processor (DSP), application specific integrated circuit (ASIC), field programmable gate array (FPGA) or other programmable logic device, discrete gate or transistor logic devices, discrete hardware components. The disclosed methods, steps and logical block diagrams in embodiments of the present invention may be implemented or executed. The general-purpose processor may be a microprocessor or the processor may be any conventional processor or the like.

The peripheral interface couples various input/output devices to the processor and the memory. In some embodiments, the peripheral interface, processor, and memory controller may be implemented in a single chip. In other examples, they can be implemented by separate chips, respectively.

The input/output unit is used for providing input data to a user to realize interaction between the user and the terminal device. The input/output unit may be, but is not limited to, mouse, keyboard, etc.

The audio unit provides an audio interface to a user, which may include one or more microphones, one or more speakers, and audio circuitry.

The display unit provides an interactive interface (e.g., a user operation interface) between the user terminal and the user or is used for displaying image data to the user for reference. In this embodiment, the display unit may be a liquid crystal display or a touch display. If it is a touch display, it can be a capacitive touch screen or a resistive touch screen that supports single-point and multi-point touch operations. Supporting single-point and multi-point touch operations means that the touch display can sense touch operations generated simultaneously from one or more positions on the touch display, and submit the sensed touch operations to the processor for calculation and processing.

In various embodiments and implementations provided by the present invention, it should be understood that the disclosed devices, systems and methods can also be implemented in other ways. The above-described apparatus, system and method embodiments are only schematic. For example, the flow charts and block diagrams in the drawings show the architecture, functions and operations of possible implementations of systems, methods and computer program products according to various embodiments of the present invention. In this regard, each block in the flowchart or block diagram may represent a module, program segment, or portion of code that contains one or more executable instructions for implementing the specified logical functions. It should also be noted that in some alternative implementations, the functions noted in the blocks may also occur in a different order than that noted in the figures. For example, two consecutive blocks may actually be executed substantially in parallel, and they may sometimes be executed in the reverse order, depending on the function involved. It should also be noted that each block in the block diagrams and/or flowchart illustrations, and combinations of blocks in the block diagrams and/or flowchart illustrations, can be implemented by special purpose hardware-based systems that perform specified functions or acts, or can be implemented by combinations of special purpose hardware and computer instructions.

In addition, each functional module in each embodiment of the invention can be integrated together to form an independent part, each module can exist independently, or two or more modules can be integrated to form an independent part.

Alternatively, it may be implemented in whole or in part by software, hardware, firmware, or any combination thereof. When implemented using software, it may be implemented in whole or in part in the form of a computer program product. The computer program product comprises one or more computer instructions. When the computer program instructions are loaded and executed on a computer, the processes or functions according to the embodiments of the present invention are generated in whole or in part. The computer may be a general-purpose computer, a special purpose computer, a computer network, or other programmable apparatus. The computer instructions may be stored in a computer-readable storage medium or transmitted from one computer-readable storage medium to another. For example, the computer instructions may be transmitted from one website site, computer, server or data center to another website site, computer, server or data center by wired (e.g., coaxial cable, optical fiber, digital subscriber line (DSL)) or wireless (e.g., infrared, wireless, microwave, etc.). The computer-readable storage medium may be any available medium that a computer can access or a data storage device such as a server, a data center, or the like that includes one or more available media integration. The usable medium may be a magnetic medium (e.g., floppy disk, hard disk, magnetic tape), an optical medium (e.g., DVD), or a semiconductor medium (e.g., Solid State Disk (SSD)) or the like.

What is claimed is:

1. An assisted dental beautification method, comprising:
obtaining information for dental beautification by shooting or receiving a video of a patient's mouth;
selecting a representative picture from the video of the patient's mouth, selecting corresponding positions of teeth to be beautified from the representative picture, and generating an image of beautified teeth at the corresponding positions, to obtain a first beautified reference picture, wherein the representative picture comprises a front view, a left side view, and a right side view, selected automatically according to a process comprising:
comparing a face of each frame with a standard facial model, and calculating a face offset angle, to obtain candidate pictures for the front, left, and right side views;
extracting an oral cavity area in the candidate pictures, calculating gray scale pictures, multiplying two gray scale differences in each pixel area of the gray scale pictures, and accumulating pixel by pixel to calculate a score according to the formula:

$$D(f)=\Sigma y \Sigma x |f(x,y)-f(x+1,y)|*|f(x,y)-f(x,y+1)|;$$

wherein x and y represent an abscissa and an ordinate of each pixel; and
selecting one of the front, left, and right views with a highest score from the candidate pictures to obtain the representative picture;
transmitting the video of the patient's mouth to a server, calculating information about the teeth to be beautified in the video of the patient's mouth using the server, and sending the information about the teeth to be beautified to a user terminal, to obtain a second beautified reference picture; and displaying the first and second beautified reference pictures to the patient for selection.

2. A user terminal function module, user terminal software, and/or a user terminal application program for implementing the assisted dental beautification method according to claim 1.

3. A server function module, server software, and/or a server application for implementing the assisted dental beautification method according to claim 1.

4. An assisted dental beautification method, comprising:
obtaining information for dental beautification by shooting or receiving a video of a patient's mouth;
selecting a representative picture from the video of the patient's mouth, selecting corresponding positions of teeth to be beautified from the representative picture, and generating an image of beautified teeth at the corresponding positions in a first beautified reference picture, wherein the representative picture comprises a front view, a left side view, and a right side view, selected automatically according to a process comprising:
comparing a face of each frame with a standard facial model, and calculating a face offset angle, to obtain candidate pictures for the front, left, and right side views;
extracting an oral cavity area in the candidate pictures, calculating gray scale pictures, multiplying two gray scale differences in each pixel area of the gray scale pictures, and accumulating pixel by pixel to calculate a score according to the formula:

$$D(f)=\Sigma y \Sigma x |f(x,y)-f(x+1,y)|*|f(x,y)-f(x,y+1)|;$$

wherein x and y represent an abscissa and an ordinate of each pixel; and
selecting one of the front, left, and right views with a highest score from the candidate pictures to obtain the representative picture;
and obtaining the first beautified reference picture comprises:
determining whether teeth that are symmetrical with the teeth to be beautified need beautification, and if not, performing Process A and optionally Process B, and if so, performing Process B, wherein Process A comprises:
calculating a width and a height of the teeth to be beautified, and cutting the symmetrical teeth to the teeth to be beautified according to contour to obtain a replacement teeth picture;
turning over a horizontal mirror picture of the replacement teeth picture and performing scaling processing, wherein a width and a height of teeth in a scaled replacement teeth picture is consistent with the width and height of the teeth to be beautified; and
pasting the scaled replacement teeth picture on the corresponding positions of the representative picture to obtain a first beautified reference picture I; and
Process B comprises:
selecting candidate teeth models from a teeth model database according to an age, gender and teeth corresponding positions of the patient;
selecting a replacement tooth model with a closest color from the candidate teeth models according to a color of adjacent and unselected teeth of the teeth to be beautified;
(re)calculating the width and the height of the teeth to be beautified, and scaling teeth pictures of a front angle of the replacement tooth model to the width and the height of the teeth to be beautified; and
pasting the scaled teeth pictures to the corresponding positions in the representative picture to obtain first beautified reference pictures II;
transmitting the video of the patient's mouth to a server, calculating information about the teeth to be beautified in the video of the patient's mouth using the server, and sending the information about the teeth to be beautified to a user terminal, to obtain a second beautified reference picture; and
displaying the first and second beautified reference pictures to the patient for selection.

5. A user terminal function module, user terminal software, and/or a user terminal application program for implementing the teeth beautification assisting method according to claim 4.

6. An assisted dental beautification method, comprising:
obtaining information for dental beautification by shooting or receiving a video of a patient's mouth;
selecting a representative picture from the video of the patient's mouth, selecting corresponding positions of teeth to be beautified from the representative picture, and generating an image of beautified teeth at the corresponding positions to obtain a first beautified reference picture, wherein the representative picture comprises a front view, a left side view, and a right side view, selected automatically according to a process comprising:
comparing a face of each frame with a standard facial model, and calculating a face offset angle, to obtain candidate pictures for the front, left, and right side views;
extracting an oral cavity area in the candidate pictures, calculating gray scale pictures, multiplying two gray scale differences in each pixel area of the gray scale pictures, and accumulating pixel by pixel to calculate a score according to the formula:

$$D(f)=\Sigma y \Sigma x |f(x,y)-f(x+1,y)|*|f(x,y)-f(x,y+1)|;$$

wherein x and y represent an abscissa and an ordinate of each pixel; and
selecting one of the front, left, and right views with a highest score from the candidate pictures to obtain the representative picture;
the corresponding positions comprise teeth numbers as follows: outward from a center line of the face, right maxillary teeth are sequentially numbered from 11 to 1m, left maxillary teeth are sequentially numbered from 21 to 2m, left mandibular teeth are sequentially numbered from 31 to 3m, and right mandibular teeth are sequentially numbered from 41 to 4m, wherein m is a number of from 1 to 8, the teeth 1m and 2m are symmetrical to each other, and the teeth 3m and 4m are symmetrical to each other, and obtaining the first beautified reference picture comprises:
determining whether teeth that are symmetrical with the teeth to be beautified need beautification, and if not, performing Process A and optionally Process B, and if so, performing Process B, wherein Process A comprises:
calculating a width and a height of the teeth to be beautified, and cutting the symmetrical teeth to the teeth to be beautified according to contour to obtain a replacement teeth picture;

turning over a horizontal mirror picture of the replacement teeth picture and performing scaling processing, wherein a width and a height of teeth in a scaled replacement teeth picture is consistent with the width and height of the teeth to be beautified; and pasting the scaled replacement teeth picture on the corresponding positions of the representative picture to obtain a first beautified reference picture I; and Process B comprises:

selecting candidate teeth models from a teeth model database according to an age, gender and teeth corresponding positions of the patient;

selecting a replacement tooth model with a closest color from the candidate teeth models according to a color of adjacent and unselected teeth of the teeth to be beautified;

(re)calculating the width and the height of the teeth to be beautified, and scaling teeth pictures of a front angle of the replacement tooth model to the width and the height of the teeth to be beautified; and pasting the scaled teeth pictures to the corresponding positions in the representative picture to obtain first beautified reference pictures II;

transmitting the video of the patient's mouth to a server, calculating information about the teeth to be beautified in the video of the patient's mouth using the server, and sending the information about the teeth to be beautified to a user terminal, to obtain a second beautified reference picture; and displaying the first and second beautified reference pictures to the patient for selection.

7. An assisted dental beautification method as claimed in claim 6, characterized in that the information of the teeth to be beautified includes position information of the teeth to be beautified, and the server calculates the position information by a process comprising:

decoding the video of the patient's mouth to obtain key frame images and non-key frame images;

for the key frame images, locating coordinates of key points and calculating the teeth positions using a cascade convolutional neural network (CNN); and for the non-key frame images, calculating the teeth positions according to the coordinates of the key points using a Lucas-Kanade sparse optical flow algorithm.

8. An assisted dental beautification method as claimed in claim 7, characterized in that for the key frame images, calculating the teeth positions comprises:

carrying out face detection on the key frame images using a face detector based on Haar features in an OpenCV vision library, then intercepting detected face images and normalizing to 128*128 size;

setting a CNN network of Level 1 to be 128 in width, 128 in height and 3 in image channel, wherein each convolution layer in the CNN network is followed by an activation layer that uses a Sigmoid function as an activation function, and the CNN network includes two final layers that are full connection layers;

inputting normalized face images into the CNN network of Level 1, and selecting coordinate values of 50 teeth key points from the teeth having tooth numbers 11-14, 21-24, 31-34 and 41-44, wherein an output of Level 1 comprises the 50 teeth coordinate values, 30 coordinate values of lip key points, 1 coordinate value of nose key points and 2 coordinate values of eye key points;

taking an image of 18*18 pixels in size from each tooth having tooth numbers 11-14, 21-24, 31-34 and 41-44 as an input to Level 2 of the CNN network, and an output of the CNN network Level 2 comprises 4 key points re-predicted around each tooth to obtain coordinate values of the 50 teeth key points, wherein adjacent teeth share one key point coordinate, and coordinate values of the shared key point coordinates are an average value of two teeth predictions;

determining numbers of four key points around the teeth according to the tooth numbers of the teeth to be beautified;

obtaining four key point coordinates around the teeth to be beautified according to output coordinate values of the 50 teeth key points; and obtaining the position information of the teeth in the key frames according to the four key point coordinates around the teeth to be beautified.

9. An assisted dental beautification method as claimed in claim 8, characterized in that calculating the teeth positions according to the coordinates of the key points by the Lucas-Kanade sparse optical flow algorithm comprises tracking the non-key frames by a process comprising:

selecting an $i^{th}$ frame as a first frame for initialization, predicting a position of an $i+1^{th}$ frame by a position of the $i^{th}$ frame, predicting a position of an $i+2^{th}$ frame by the position of the $i+1^{th}$ frame, and so on to an $i+(k/2)^{th}$ frame, wherein the $i^{th}$ and the $i+k^{th}$ frames are the adjacent key frames, and the $i+1^{th}$ to the $i+(k-1)^{th}$ frames are the non-key frames; and selecting the $i+k^{th}$ frame as a first frame for a subsequent initialization, predicting a position of the $i+k-1^{th}$ frame from a position of the $i+k^{th}$ frame, predicting a position of the $i+k-2^{th}$ frame from the position of the $i+k-1^{th}$ frame, and so on to an $i+(k/2)+1^{th}$ frame.

10. An assisted dental beautification method as claimed in claim 9, characterized in that tracking the non-key frames smooths each key point in the non-key frame images by a process comprising:

choosing a quadratic equation $f(z)=b_0+b_1z+b_2z^2$ for any key point;

bringing in values of two key frames and all non-key frames between the two key frames, $(h, d_h)$, $h \in [0,H]$, and renumbering the key frames and the non-key frames between the two key frames by taking smaller index values in the two key frames as the $0^{th}$ frame, wherein H is a sum of the two key frames plus a number of the non-key frames between the two key frames, h represents an $h^{th}$ frame after renumbering, and $d_h$ represents a coordinate value of a key point in the $h^{th}$ frame;

defining a loss function $Q=\Sigma_A(f(z)-b_0-b_1z-b_2z^2)$, $h \in [0, H]$, respectively bringing an abscissa z value and an ordinate f(z) value into the loss function Q, obtaining values of $b_0$, $b_1$ and $b_2$ to obtain two different curve equations, wherein the values of $b_0$, $b_1$ and $b_2$ minimize the value of Q; and bringing h into two curve equations, and calculating coordinate values of the smoothed key points in the non-key frames.

11. A user terminal function module, user terminal software, and/or a user terminal application program for implementing the assisted dental beautification according to claim 10.

12. A server function module, server software, and/or a server application for implementing the assisted dental beautification method according to claim 10.

13. A user terminal function module, user terminal software, and/or a user terminal application program for implementing the assisted dental beautification method according to claim 9.

14. A server function module, server software, and/or a server application for implementing the assisted dental beautification method according to claim 9.

15. An assisted dental beautification method as claimed in claim 8, characterized in that the information of the teeth to be beautified in the videos of patient's mouths includes color information, and calculating the color information includes:
  intercepting entire teeth area in each frame according to the output coordinate values of the 50 teeth key points;
  selecting LAB space, and calculating an average value of all pixels in a whole teeth region under L, A and B channels respectively, to obtain (La_i, Aa_i, Ba_i), wherein a represents the whole teeth region, and represents the $i^{th}$ frame;
  based on a LAB value (La_front, Aa_front, Ba_front) of the front view, calculating a change value of each channel in each frame forward and backward, respectively, according to the formula:

$$\begin{cases} La\_sub = (La\_i - La\_front)/La\_front; \\ Aa\_sub = (Aa\_i - Aa\_front)/Aa\_front; \text{ and} \\ Ba\_sub = (Ba\_i - Ba\_front)/Ba\_front; \end{cases}$$

calculating a LAB channel color value of a $j^{th}$ pixel point of the teeth to be beautified in an $i^{th}$ frame image according to the formula:

$$\begin{cases} Lj\_i = Lj\_front + Lj\_front * La\_sub; \\ Aj\_i = Aj\_front + Aj\_front * Aa\_sub; \\ Bj\_i = Bj\_front + Bj\_front * Ba\_sub. \end{cases}$$

16. A user terminal function module, user terminal software, and/or a user terminal application program for implementing the assisted dental beautification method according to claim 15.

17. A server function module, server software, and/or a server application for implementing the assisted dental beautification method according to claim 15.

18. A user terminal function module, user terminal software, and/or a user terminal application program for implementing the assisted dental beautification method according to claim 8.

19. A server function module, server software, and/or a server application for implementing the assisted dental beautification method according to claim 8.

* * * * *